United States Patent [19]
McCaffrey

[11] Patent Number: 4,726,679
[45] Date of Patent: Feb. 23, 1988

[54] FLAME ATOMIC ABSORPTION SPECTROPHTOMETER INCLUDING APPARATUS AND METHOD FOR LOGARITHMIC CONVERSION

[75] Inventor: John T. McCaffrey, Hamden, Conn.

[73] Assignee: The Perkin-Elmer Corporation, Norwalk, Conn.

[21] Appl. No.: 835,145

[22] Filed: Mar. 3, 1986

[51] Int. Cl.⁴ .............................. G01N 21/72
[52] U.S. Cl. ..................... 356/315; 356/325
[58] Field of Search ............ 356/315, 326, 319, 323, 356/325

[56] References Cited

U.S. PATENT DOCUMENTS

| | | | |
|---|---|---|---|
| 3,499,160 | 3/1970 | Gordon | 356/319 X |
| 3,522,739 | 8/1970 | Coor et al. | 356/325 X |
| 3,586,441 | 6/1971 | Smith et al. | 356/315 X |
| 4,070,112 | 1/1978 | Tsunazawa et al. | 356/319 |

FOREIGN PATENT DOCUMENTS

| | | | |
|---|---|---|---|
| 58-92931 | 6/1983 | Japan | 356/315 |
| 58-127149 | 7/1983 | Japan | 356/325 |

Primary Examiner—Vincent P. McGraw
Attorney, Agent, or Firm—Francis L. Masselle; Herbert S. Ingham; Edwin T. Grimes

[57] ABSTRACT

The optical measurement signals in a flame atomic absorption spectrophotometer are first amplified in a substantially linear variable gain amplifier. The gain of the variable gain amplifier is adjusted to provide a predetermined magnitude of output signal during a calibration phase of the spectrophotometer. The resultant output signals from the variable gain amplifier are then converted to a logarithmic function in a logarithmic amplifier during optical absorption measurements.

8 Claims, 2 Drawing Figures

FLAME ATOMIC ABSORPTION SPECTROPHTOMETER INCLUDING APPARATUS AND METHOD FOR LOGARITHMIC CONVERSION

FIELD OF THE INVENTION

The present invention relates to an amplifier system for a flame atomic absorption spectrophotometer which includes a logarithmic converter, and to a logarithmic conversion method which is especially useful in a low cost flame atomic absorption spectrophotometer.

BACKGROUND OF THE INVENTION

In atomic absorption spectroscopy, the measurement of the absorption of a radiation beam at a characteristic resonant spectral line for a particular element yields a measure of the concentration of that element in an original sample solution. Presently, one of the most common techniques for atomizing an element for purposes of the absorption measurement is by introducing a liquid sample solution of the element of interest into a gas burner wherein droplets of the solution are vaporized and the elements ultimately atomized, so as to form in the path of the apparatus radiation beam, a substantial quantity of the element of interest in its atomic state. A sample light beam, which originates from a line-emitting light source, and which includes a resonance line of the element to be measured, is directed thorugh the flame. The desired element in the sample absorbs the resonance lines characteristic of the element and the emerging light beam is directed to a monochromator and thence to a detector which measures the degree to which the desired element absorbs the resonance lines of the sample beam. This absorption degree represents the amount of desired element in the sample substance.

Atomic absorption spectrophotometer apparatus has been higly developed and is highly accurate. However, it is also quite expensive.

Accordingly, one object of the present invention is to provide an atomic absorption spectrophotometer apparatus which is substantially reduced in cost with very little compromise in the accuracy of the instrument.

One of the problems in producing an accurate low cost instrument is that the system must respond to rapidly changing signals, and must operate over a wide range of optical signal intensity. Also, it is desirable, in a low cost instrument to employ a silicon photodiode rather than a photomultiplier tube as the photoresponsive device. One of the problems in achieving a high accuracy is that it is desired to use different lamps for different optical tests which provide widely varying output currents from the photodiode. For instance, if an arsenic gaseous discharge lamp is used, the photodiode currents are very low, being in the range of about $1 \times 10^{-10}$ to $1 \times 10^{-14}$ amperes. However, when chromium gaseous discharge lamps are used, the current is about $2 \times 10^{-8}$ amperes. This represents six orders of dynamic range. The usual arrangement, where a logarithmic function amplifier is required, is to connect the logarithmic amplifier directly to the photoresponsive device so that the electrical output of the photoresponsive device is directly amplified and converted to logarithmic form. However, providing a highly accurate logarithmic converter which is operable over six orders of dynamic range is expensive and complicated.

Accordingly, it is another object of the present invention to provide a system including a logarithmic amplifier, or a logarithmic converter, which is inexpensive and which will very accurately deal with electro-optical signals of widely varying amplitudes.

Further objects and advantages of the invention will be apparent from the following description and the accompanying drawings.

SUMMARY OF THE INVENTION

In carrying out the invention there is provided a method for providing logarithmic conversion of the optical measurement signals in a flame atomic absorption spectrophotometer comprising first amplifying the signals in a substantially linear variable gain amplifier, adjusting the gain of the variable gain amplifier to provide a predetermined magnitude of output signal during a calibration phase of the spectrophotometer, and then converting the resultant output signals from the variable gain amplifier to a logarithmic function in a logarithmic amplifier during optical absorption measurements.

DETAILED DESCRIPTION OF THE INVENTION

Figure 1:
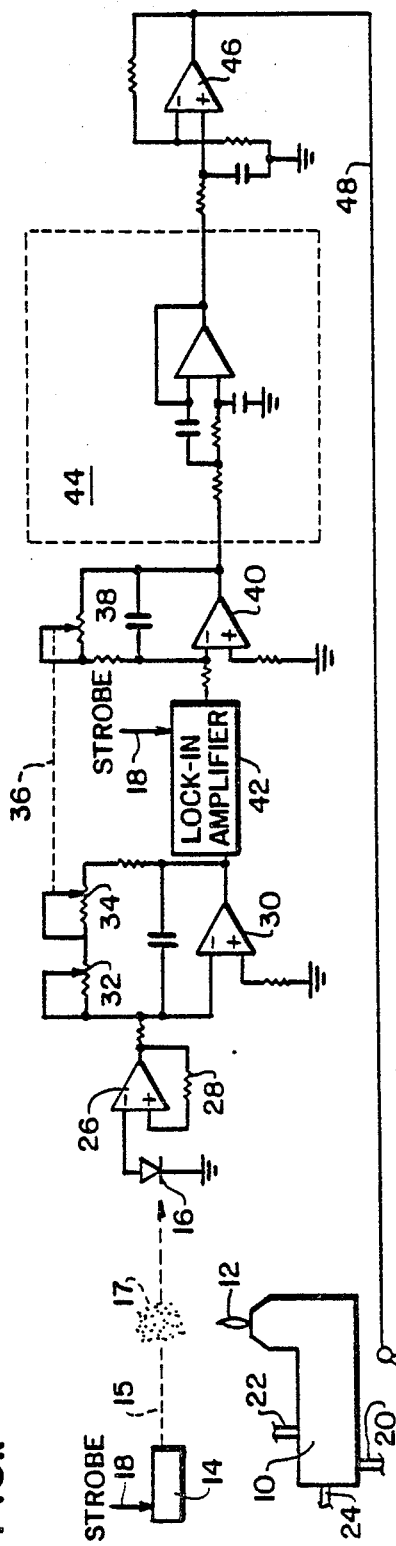
FIG. 1 is a schematic diagram of a preferred embodiment of the present invention.

Referring more particularly to FIG. 1, the burner 10 for a flame atomic absorption spectrophotometer is illustrated having a flame at 12 and a light source 14, which is preferably a hollow cathode gaseous discharge lamp. Optical energy from a beam 15 from the source 14 is absorbed by the vaporized atoms 17 of a substance to be measured. The atoms are vaporized in the flame 12. The remaining light is received by a photo-optical detector consisting of a photodiode 16. In a preferred embodiment, the photodiode is a silicon photodiode such as a model S1227-16BQ available from Hamamatsu Corporation, 420 South Ave. CN420, Middlesex, N.J. 08846-258M, U.S.A.

The optical signal from the light source 14 is preferably switched on and off in a rapid sequence by a strobe signal indicated at 18 from a strobe control source which is not illustrated. Alternatively, the optical signal may be interrupted by a rotating shutter device which preferably has two or more shutter blades. The rapid interruptions of the illumination source provide a basis for continuously calibrating the instrument to detect only the difference between the ambient illumination and the total illumination including the ambient illumination plus the optical signal from source 14.

The atomic absorption spectrophotometer burner 10 includes inlets at 20, 22, and 24 for respectively receiving an oxidant gas, a fuel gas, and a liquid solution of a substance to be measured.

The electrical signal from the photodiode detector 16 is amplified in an amplifier 26, which also serves as a current-to-voltage converter. Preferably, the feedback resistor 28 of the amplifier 26 is quite high, in the order of 100 megohms, in order to provide a high voltage amplification. The signal is then applied to a variable gain amplifier 30 which includes two variable resistors 32 and 34 in its feedback circuit. The variable resistor 32 preferably has a smaller total resistance than variable resistor 34. Variable resistor 32 is therefore used for a fine adjustment, and variable resistor 34 for a coarse adjustment. The variable contact of resistor 34 is preferably mechanically coupled, as indicated at 36, with a variable contact of a variable resistor 38 in a later stage amplifier 40 in order to achieve an even greater range in the coarse amplification adjustment.

Between the amplifiers 30 and 40, there is provided a lock-in amplifier 42. The lock-in amplifier 42 receives, and is locked into, the strobe reference signal at 18 which switches the illumination source 14 on and off. The lock-in amplifier operated in two modes to measure the ambient light when the illumination source 14 is off, and then to measure the total signal when the illumination source 14 is on. The amplifier then subtracts the ambient light signal from the total signal to obtain only the meaningful signal difference as picked up by the photodiode 16.

After the lock-in amplifier, the signal is sent through the variable gain amplifier 40 to a Butterworth filter 44, which is basically a low pass filter. This smooths the pulsed output from lock-in amplifier 46. The signal is then amplified in a fixed gain amplifier 46, and carried through a connection 48 to a logarithmic amplifier. The logarithmic amplifier includes two operational amplifiers 50 and 52, and a bipolar transistor device 54 which serves as a nonlinear feedback element to provide the logarithmic function.

The logarithmic amplifier may be referred to as a logarithmic converter, and is of a type which is sometimes referred to as a log ratio amplifier. The preferable circuit configuration corresponds closely to that which was shown in FIG. 1 in an article entitled "Logarithmic Convertors" by Robert C. Dobkin which appeared in the IEEE Spectrum for November 1969, on pages 69–72.

The signal current is applied at a terminal 49 and thus through an input resistor 56. The transistor device 54 includes two bipolar transistors 60 and 62. The transistor 60 serves as the nonlinear feedback element in the feedback circuit of the amplifier 50. Negative feedback is applied to the emitter of transistor 60 through a voltage divider consisting of resistors 64 and 66 and the emitter-base junction of transistor 62. This forces the collector current of transistor 60 to equal the current through the input resistor 56. Transistor 62 is used as the feedback element of the operational amplifier 52. Negative feedback forces the collector current of transistor 62 to equal the current through an input resistor 68 which is supplied with a constant voltage from a voltage reference source as indicated at 70.

Since the collector current of transistor 62 remains constant, the emitter-base voltage also remains constant. Therefore, only the base-to-emitter voltage of transistor 60 varies with the change of input current. However, the output voltage at connection 72 is a function of the difference in emitter-base voltages of transistors 60 and 62. The transistors 60 and 62 are matched in characteristics and are preferably a part of the same device, and in the same enclosure, and therefore subjected to the same thermal environment.

Resistor 66 is preferably a thermistor, in order to provide temperature compensation to the operation of the system. With that arrangement, the output voltage at connection 72 is a temperature compensated logarithmic function of the input voltage at the inverting input of amplifier 50.

In order to promote stability, a capacitor 76 is connected between the input and the output. Also, an emitter degeneration resistor 78 is included to limit the loop gain at high input levels.

This logarithmic converter provides for an accurate logarithmic conversion over a wide range. However, the accuracy and the range of the system is substantially improved by applying the logarithmic conversion only to the useful component of the signal, after zero corrections have been applied to the signal by the adjustable gain amplifiers 30 and 40, and by the subtraction of the ambient light signal by the lock-in amplifier 42.

While a particular preferred logarithmic amplifier or logarithmic converter circuit is shown and described, it will be understood that other logarithmic converter circuits may be employed, if desired.

The output 72 from the logarithmic converter is connected through an amplifier 73 to a signal utilization device 74. The signal utilization device 74 may typically be an oscilloscope, or a recorder, or both.

Figure 2:
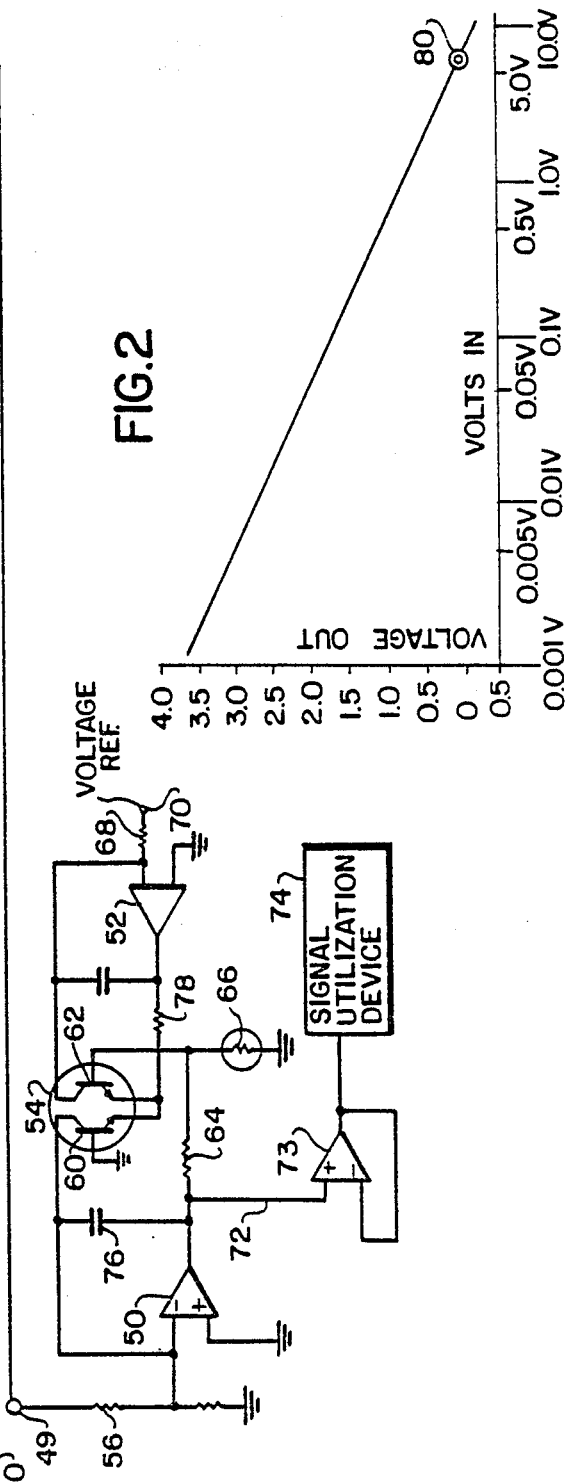
FIG. 2 is a plot showing the logarithmic output obtainable from the system illustrated in FIG. 1.

FIG. 2 is a curve sheet showing the logarithmic amplifier response in a preferred embodiment of the invention. The output voltage is plotted as the ordinate, and the input voltage as the abscissa on a logarithmic scale. The output function provides a direct reading of the absorbance of illumination in the atomic absorption spectrophotometer.

In operation, the variable gain amplifiers 30 and 40 are preferably adjusted so that the input voltage to the logarithmic converter at terminal 49 is approximately 6 volts. This voltage is sometimes referred to below as a "scaling" voltage. When this condition is achieved, the output voltage, as amplified by the fixed gain amplifier 73 to the utilization device 74 is zero volts, indicating zero absorption. This adjustment is accomplished using a calibration liquid sample at burner 10 which does not contain any constituents providing any absorbance. The 6-volt zero output absorbance point is indicated in FIG. 2 at 80. As seen in FIG. 2, the logarithmic converter provides for a logarithmic conversion of the signal over a range of substantially four decades.

While this invention has been shown and described in connection with a particular preferred embodiment, various alterations and modifications will occur to those skilled in the art. Accordingly, the following claims are intended to define the valid scope of this invention over the prior art, and to cover all changes and modifications falling within the true spirit and valid scope of this invention.

What is claimed is:

1. In a flame atomic absorption spectrophotometer that includes a light source for providing measurement illumination for absorbance by a material being analyzed to produce an optical signal which sequal happens to include ambient illumination, a signal processing system comprising in combination:
   interrupting means for periodically interrupting said measurement illumination as a means of producing an ambient signal for standardizing for said ambient illumination;
   a photoresponsive diode device receptive of said optical signal;
   an operator adjustable variable gain amplifier including a first variable gain stage operatively connected to said diode device and further including a second variable gain stage;
   a lock-in amplifier operatively connected between said first variable gain stage and said second variable gain stage and being connected for synchronization with said interrupting means, and being operable to detect said ambient signal received during interruption of said measurement illumination and subtract said ambient signal from said optical signal received when said measurement illumination is not interrupted to provide an output signal corrected for said ambient illumination, said second variable gain stage being receptive of said output signal; and a logarithmic amplifier operatively connected to said second variable gain stage to provide a logarithmic output signal;

said variable-gain amplifier being adjustable to supply a predetermined calibration input voltage to said logarithmic amplifier during a calibration operation phase of said signal processing system.

2. A system as claimed in claim 1 wherein said light source comprises a hollow cathode gaseous discharge lamp.

3. A system as claimed in claim 1 wherein said second variable gain stage is connected with an interconnection to said first variable gain stage to provide for common adjustment of gain by both of said stages.

4. A system as claimed in claim 1 wherein there is provided a low pass Butterworth filter connected in circuit between said lock-in amplifier and said logarithmic amplifier.

5. A system as claimed in claim 1 wherein said logarithmic amplifier comprises at least one operational amplifier with a bipolar solid state element connected in a feedback circuit for said operational amplifier to provide for a logarithmic function.

6. A system as claimed in claim 5 wherein said bipolar solid state element in said feedback circuit comprises a transistor.

7. A system as claimed in claim 6 wherein said logarithmic amplifier comprises a matched pair of transistors in a common enclosure and a matched pair of operational amplifiers, said operational amplifiers and said matched transistors being arranged in a current-balanced logarithmic converter amplifier circuit.

8. A system as claimed in claim 7 wherein there is provided a temperature compensating resistor connected in said current-balanced circuit to provide an automatic adjustment in a voltage bias on said transistors to compensate for changes in the operation of said transistors in response to temperature changes.

* * * * *

UNITED STATES PATENT AND TRADEMARK OFFICE
CERTIFICATE OF CORRECTION

PATENT NO. : 4,726,679
DATED : February 23, 1988
INVENTOR(S) : John T. McCaffrey It is certified that error appears in the above-identified patent and that said Letters Patent are hereby corrected as shown below:

IN THE CLAIMS:

Column 4, line 52, delete "sequal" and insert --signal--.

Signed and Sealed this

Twentieth Day of September, 1988

Attest:

DONALD J. QUIGG

Attesting Officer        Commissioner of Patents and Trademarks